Figure 1:
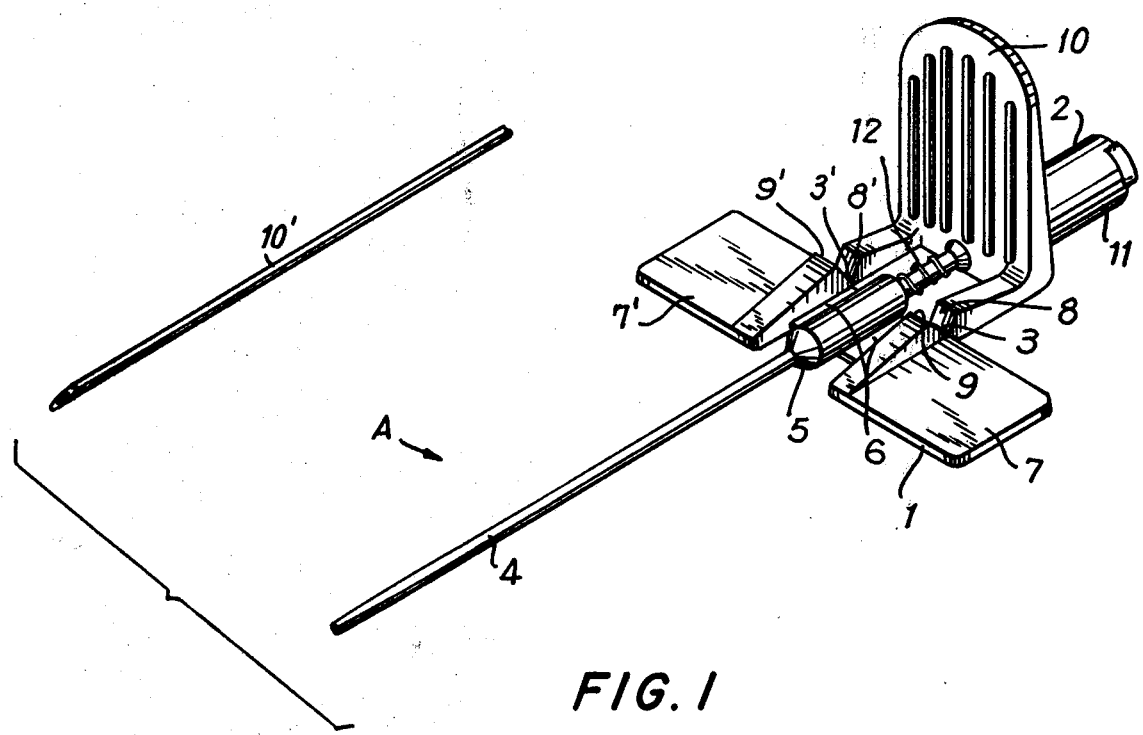

United States Patent [19]

Fuchs

[11] 4,161,177

[45] Jul. 17, 1979

[54] CATHETER ATTACHMENT

[75] Inventor: Heinz Fuchs, Melsungen, Fed. Rep. of Germany

[73] Assignee: Intermedicat GmbH, Emmenbrucke, Switzerland

[21] Appl. No.: 769,335

[22] Filed: Feb. 11, 1977

[30] Foreign Application Priority Data

Feb. 12, 1976 [CH] Switzerland ............... 1725/76

[51] Int. Cl.² ............................................. A61M 5/00
[52] U.S. Cl. .................... 128/214.4; 128/348; 128/DIG. 16
[58] Field of Search ............... 128/214 R, 214.4, 221, 128/348, DIG. 16, DIG. 26

[56] References Cited

U.S. PATENT DOCUMENTS

| 3,769,975 | 11/1973 | Nimoy et al. | 128/214.4 |
| 3,851,647 | 12/1974 | Monestere et al. | 128/214.4 |
| 4,046,144 | 9/1977 | McFarlane | 128/214.4 |

FOREIGN PATENT DOCUMENTS 1534118  6/1968  France ......................... 128/214.4

Primary Examiner—Dalton L. Truluck
Attorney, Agent, or Firm—Curtis, Morris & Safford

[57] ABSTRACT

A catheter attachment for introducing a flexible catheter into a blood vessel includes front and rear attachment sections and a hinge for pivotally connecting these sections. A flexible catheter is mounted in the attachment sections and the rear attachment section includes a connection for placing the catheter in communication with a transfusion device. As a result the rear attachment section and the portion of the catheter therein may move with respect to the front attachment section, which is taped or otherwise secured to the patient, without disturbing the portion of the catheter tube extending from the front attachment section into the patient.

17 Claims, 2 Drawing Figures

CATHETER ATTACHMENT

The present invention relates to catheter attachments and more paticularly to a catheter attachment for use in inserting a flexible catheter into a blood vessel and preventing disturbance of the portion of the catheter in the blood vessel.

Depending on the place of puncture and introduction and also on the indicated therapeutic procedure being conducted, catheter devices, which usually consist of biologically inert synthetic materials, are formed in many different designs. A preferred type of catheter presently used for intravenous as well as intra-arterial introduction of fluids consists of a plastic tube or catheter having a cone attachment and having a length of usually up to 10 cm. A metal cannula or needle is received in this tube and its ground or sharpened free end projects beyond the end of the plastic catheter. When using this type of catheter structure the blood vessel is punctured and the metal cannula is removed after the vessel lumen has been reached. The plastic catheter remains in the blood vessel and serves as a catheter for introducing an infusion solution.

In many cases the catheter remains in the blood vessel for several days. Thus the method of fixation or securement of the catheter on the patient's skin is of great importance; and a great number of methods of catheter attachments have been developed for this purpose. Typically such fixation aides include a molded part on or adjacent the cone attachment at the rear end of the catheter tube that serves to form the connection to transfusion devices. The usual catheter attachments have a square or round section and are fixed or secured to the skin with the aid of adhesive tape. Supporting plates are often placed below the catheter on the skin which project laterally at right angles to the catheter to aid in supporting it firmly in place.

A common feature of previously proposed catheter designs is that pressure or tension exerted on the catheter attachment is more or less strongly transferred to the flexible catheter itself which may then result in a dislocation of the catheter in the patient. If this occurs again and again, for example with restless patients, the inner wall of the blood vessel and the place of puncture will be irritated and inflamed. In addition to tension or pressure on the catheter in the direction of its longitudinal axis, lateral deflections of the catheter are also critical and must be avoided, because of its direct effect on the patient since such deflections may cause the catheter to bend and block the flow of lumen of the blood vessel in which it is inserted. Certain synthetic materials that would be suitable as catheter material because of their relatively good physiological tolerability, are especially susceptible to such bending, and possess only a low restoring capability after a deformation by bending. Thus while such materials are desirable for use in manufacturing catheters their use has been limited because of these problems.

Besides by the behavior of the catheter as determined by the properties of the material from which it is formed, the susceptibility to bending of vein indwelling catheters is also influenced by the shaping of the cone attachment for the connection to transfusion devices. For example, due to the standardized cone dimensions, a cone attachment provided with a circular section has a diameter of 6 mm or more, and the catheter tube is centrally fastened therein. If a puncture is made in the patient's skin with the vein indwelling cannula being introduced into a blood vessel somewhat inclined towards the body surface, and if the cone attachment is fixed to the catheter and the patient, it may happen that no supporting surface is available for the portion of the catheter protruding from the skin and extending to the cone attachment; thus the catheter lies free and unsupported or guided at least over a short portion of its length and the tube may thus bend even with a slight dislocation or movement of the attachment.

It is an object of the present application to provide an improved catheter attachment for the introduction of a flexible catheter into a blood vessel.

It is another object of the invention to provide a catheter attachment in which longitudinal dislocations or movements of the catheter, caused by tension, pressure, or lateral deflections caused by shock effects on the catheter, which would result in bending of the catheter pipe, are prevented.

In accordance with an aspect of the invention, a catheter attachment for holding a catheter tube in place after insertion with the aid of a puncture cannula or needle, has two attachment parts or sections connected to each other by means of an integral flexible hinge. The front part of the catheter attachment facing the catheter tube is connected with the catheter tube frictionally and tightly and includes flat fixation plates adapted to lie on the skin of the patient and provide supports for taking the attachment to the patient's skin. The back part of the catheter attachment is used to connect the catheter to a transfusion device and is movably connected with the front part of the catheter attachment by means of the hinge. By this arrangement any forces applied to the catheter attachment originating from an infusion line connected to the catheter attachment, or from instruments or syringes inserted in the catheter or catheter attachment will not act immediately on the whole catheter attachment and be transferred further to the catheter tube, but can only move the mobile back part of the catheter attachment in the direction determined by the form of the hinge. Preferably this movement is not led over a too great deflection angle, but is limited by an angular movement of up to about 90° and preferably up to about 45°.

In spite of the movability given by the hinge, the back part of the catheter attachment may, for better handling purposes, have a holding plate standing perpendicularly to the catheter axis, to aid in the manipulation of the attachment during puncture of the skin and introduction of the indwelling catheter into the blood vessel in connection with a second holding plate that is fastened to the metallic puncture cannula or needle in the catheter tube. Although this holding plate is movable relative to the front attachment part of section because of the intermediate hinge, the rigid non-movable relation between those parts, required for the puncture, is achieved and maintained by the metal cannula or needle lying in the inner bore of the catheter and extending across the hinge between the two attachment sections during the puncture operation.

An additional feature of the catheter attachment of the invention which is important for the course of an infusion or injection is the opening or support passage in the otherwise solid shaped front attachment part. This opening is situated in an intermediate position on the supporting plate in front of the hinge, with the catheter tube being led through the opening.

With the front attachment part of the invention fixed or taped tightly on the skin, any bending strain is absorbed by the back part of the catheter attachment hanging by the hinge. This motion is checked by means of a pair of stop walls formed on the respective attachment parts to limit angular movement between the parts to a given angle. Since the usual catheter tubes consisting of thermoplastic materials show an elastic behavior and a resistance to bending sufficient for this limited flexion, bending of the catheter tube which would hinder or even stop the infusion is prevented. In cases where the material of the catheter is not stiff, a support in the form of a spiral made of metal or another material can be provided to prevent bending of the catheter tube and eliminate any disturbances.

Figure 2:
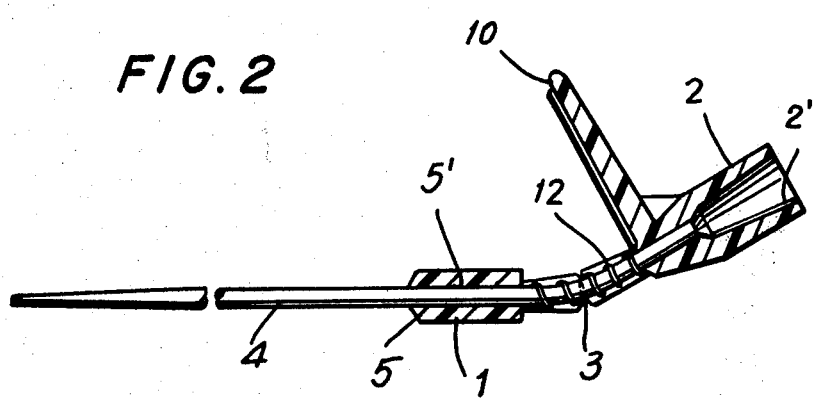

The above, and other objects, features and advantages of this invention will be apparent in the following detailed description of an illustrative embodiment which is to be read in conjunction with the accompanying drawings, wherein:

FIG. 1 is a perspective view of the catheter attachment according to the invention; and FIG. 2 is a longitudinal sectional view taken along line 2—2 of FIG. 1, showing the attachment parts in an angular relation to each other.

A catheter attachment A according to the invention has a front part or section 1 and a rear part or section 2 connected to each other by a divided hinge 3 and 3'. The hinge elements 3, 3' are integral with front and rear attachment sections and are thin plastic flexible strips molded with sections 1 and 2.

A catheter tube 4 which serves as an infusion passage is tightly secured in the front attachment section within a passage 5' in a guide 5 formed in section 1. The tight frictional engagement of the catheter in passage 5' assures that movement of back part 2 cannot have any effect on the catheter. Front attachment part 1 also includes two symmetrically arranged supporting and fixing plates 7 and 7' connected with guide piece 5 by integral crosspieces 6. These plates are used to tape the front attachment part on the patient's skin. Stop faces 8, 8', 9, 9', are formed on attachment parts 1, 2 adjacent hinges 3, 3' and they are located to engage each other when back part 2 has pivoted to a predetermined angle (e.g. 90° and preferably 45°) with respect to front part 1, thereby to limit the deflection of front part 1 and back part 2 with respect to each other.

Back part 2 includes an integral holding plate 10 which is used to aid in manipulating the attachment during skin puncture in connection with a metal cannula 10'.

Rear attachment part 2 also includes an integral attachment piece 11 having an internal core or bore 2' formed therein which is used to provide for connection with transfusion devices, syringes, etc. Optionally, attachment piece 11 may also be used for plug connections and locking connections. The metal needle 10', prior to insertion of cannula 4 in the patient is located within cannula 4 and extends therethrough across hinges 3 and through the rear part 2. The rear end of the needle may itself be secured to a separate support to aid in its insertion and removal. In any event the needle prevents parts 1 and 2 from pivoting with respect to each other during the puncture of the skin and insertion of cannula 4. After cannula 4 is inserted in the vein, the needle 10' is removed from the cannula and attachment part 2 is free to pivot.

Where catheter tube 4 is formed of a material particularly susceptible to bending, a supporting tube guide, for example in the form of a metal spiral 12 may be provided around the catheter adjacent the hinge 3 to support and reinforce the catheter. This spiral member may be embedded within the catheter to resist collapsing of the catheter or bending thereof.

FIG. 2 shows the catheter attachment in a position wherein the attachment parts 1 and 2 are at an angle to each other, limited by the slope of the stop faces adjacent to the hinge 3. Since the catheter tube 4 is tightly fixed in the guide 5 (e.g. by a tight frictional engagement) deflection of back part 2 will not cause any motion at catheter tube 4.

Although an illustrative embodiment of the present invention has been described herein with reference to the accompanying drawings, it is to be understood that the invention is not limited to that precise embodiment but that various changes and modifications may be effected therein by one skilled in the art without departing from the scope or spirit of this invention.

What is claimed is:

1. A catheter attachment for introducing a flexible catheter into a blood vessel, comprising front and rear attachment sections and means for pivotally connecting said sections, and a flexible catheter mounted in said attachment sections, said rear attachment section including means communicating with said catheter for providing communication between the catheter and a transfusion device, whereby the rear attachment section and the portion of the catheter therein may move with respect to the front attachment section without disturbing the remainder of the catheter in and extending from the front attachment section; and means for limiting angular movement of said attachment sections with respect to one another to about 90°.

2. A catheter attachment as defined in claim 1 wherein said hinge means comprises a flexible portion of the attachment element integrally formed with said front and rear attachment sections.

3. A catheter attachment as defined in claim 1 wherein said limiting means limits angular movement between said attachment sections to 45°.

4. A catheter attachment as defined in claim 1 wherein said limiting means comprise angularly related surfaces formed on said front and rear attachment sections positioned to engage each other at a predetermined angular relation between said sections to prevent further angular movement therebetween.

5. A catheter attachment as defined in claim 1 wherein said front attachment section includes an integral guide tube having a central bore formed therein receiving and frictionally engaging said catheter.

6. A catheter attachment as defined in claim 1 wherein said rear attachment piece includes a holding plate extending therefrom generally perpendicularly to the longitudinal axis of the portion of the catheter mounted in said rear attachment section.

7. A catheter attachment as defined in claim 1 wherein said front attachment section includes a pair of laterally extending flat supporting plates for use in securing the attachment to a patient.

8. A catheter attachment for introducing a flexible catheter into a blood vessel, comprising front and rear attachment sections and means for pivotally connecting said sections, and a flexible catheter mounted in said attachment sections, said rear attachment section including means communicating with said catheter for providing communication between the catheter and a transfusion device, whereby the rear attachment section and the portion of the catheter therein may move with respect to the front attachment section without disturbing the remainder of the catheter in and extending from the front attachment section; and a catheter support guide member engaged with the catheter at the portion thereof adjacent said hinge means; said support guide member comprising a metal spiral element surrounding the catheter.

9. A catheter attachment for use in introducing a flexible catheter into a blood vessel and preventing movement of the portion of the catheter inserted in the blood vessel comprising a one piece attachment element including front and rear attachment elements and an integral flexible hinge formed therebetween, and a hollow flexible catheter mounted in said attachment section including a first front end portion extending away from the first attachment section for insertion in a blood vessel, a second rear end portion mounted in said rear attachment section and a central portion located adjacent said hinge; said rear attachment section including means communicating with said rear end portion of the catheter for placing the catheter in communication with a transfusion device, whereby the rear attachment section and the portion of the catheter therein may move with respect to the front attachment section without disturbing the front end portion of the catheter in the blood vessel.

10. A catheter attachment as defined in claim 9 including means for limiting angular movement of said attachment sections with respect to one another to about 90°.

11. A catheter attachment as defined in claim 10 wherein said limiting means limits angular movement between said attachment sections to 45°.

12. A catheter attachment as defined in claim 9 wherein said limiting means comprise angularly related surfaces formed on said front and rear attachment sections positioned to engage each other at a predetermined angular relation between said sections to prevent further angular movement therebetween.

13. A catheter attachment as defined in claim 12 wherein said front attachment section includes a pair of laterally extending flat supporting plates for use in securing the attachment to a patient.

14. A catherer attachment as defined in claim 13 including an integral guide tube positioned between said flat supporting plates and having a central bore formed therein receiving and frictionally engaging said catheter.

15. A catheter attachment as defined in claim 14 wherein said rear attachment piece includes a holding plate extending therefrom generally perpendicularly to the longitudinal axis of the portion of the catheter mounted in said rear attachment section.

16. A catheter attachment as defined in claim 15 including a catheter support guide member engaged with the catheter at the portion thereof adjacent said hinge means.

17. A catheter attachment as defined in claim 16 wherein said support guide member comprises a metal spiral element surrounding the catheter.

* * * * *